United States Patent [19]

Yanagihara et al.

[11] 3,978,138

[45] Aug. 31, 1976

[54] PROCESS FOR PREPARING P-DIISOPROPYL-BENZENEDIHYDROPEROXIDE

[75] Inventors: Tadahisa Yanagihara; Toshikuni Koga; Kentaro Fukahori, all of Shin-nanyo, Japan

[73] Assignee: Toyo Soda Manufacturing Co., Ltd., Shin-nanyo, Japan

[22] Filed: Oct. 18, 1974

[21] Appl. No.: 515,870

[30] Foreign Application Priority Data

Oct. 29, 1973  Japan.......................... 48-120692

[52] U.S. Cl............................ 260/610 B; 260/610 A
[51] Int. Cl.²................................... C07C 179/02
[58] Field of Search..................... 260/610 A, 610 B

[56] References Cited
UNITED STATES PATENTS 2,715,646  8/1955  Hawkins et al.................... 260/61 B
3,190,924  6/1965  Sodomann et al.............. 260/610 B

FOREIGN PATENTS OR APPLICATIONS 727,498  4/1955  United Kingdom............ 260/610 B Primary Examiner—James O. Thomas, Jr.
Assistant Examiner—W. B. Lone
Attorney, Agent, or Firm—Oblon, Fisher, Spivak, McClelland & Maier

[57] ABSTRACT p-Diisopropylbenzene dihydroperoxide is prepared by contacting p-diisopropylbenzene with molecular oxygen, adding an alkali metal hydroxide or an alkaline earth metal hydroxide to the reaction mixture to precipitate p-diisopropylbenzenedihydroperoxide, separating p-diisopropylbenzenedihydroperoxide from the reaction mixture which creates a residual solution containing p-diisopropylbenzene and p-diisopropylbenzenemonohydroperoxide which is recycled. The residual solution resulting from the reaction mixture can also be contacted with the alkali metal hydroxide or the alkaline earth metal hydroxide.

14 Claims, No Drawings

PROCESS FOR PREPARING P-DIISOPROPYL-BENZENEDIHYDROPEROXIDE

BACKGROUND OF THE INVENTION

1. Field of the Invention:

The present invention relates to a process for preparing p-diisopropylbenzenedihydroperoxide (hereinafter referred to as DIX). More particularly, the present invention relates to a process for preparing DIX in high yield from p-diisopropylbenzene (hereinafter referred to as DIPB) or a mixture of DIPB and p-diisopropylbenzene-monohydroperoxide (hereinafter referred to as MOX).

2. Description of the Prior Art:

p-Diisopropylbenzenedihydroperoxide has been prepared by emulsifying DIPB or a mixture of DIPB and MOX in an aqueous solution of sodium cabonate and oxidizing the same with air or oxygen. The reaction mixture comprises a water phase containing sodium carbonate and an oil phase containing mainly DIX, MOX, DIPB and byproducts of high boiling materials whose structures are not known. DIX is separated from the oil phase and the residual oil phase (hereinafter referred to as a recycle solution) is further used as a starting material for the oxidation reaction.

In order to economically prepare DIX, DIX must be prepared in high yield in the above process. However, the conventional process for preparing DIX has the following disadvantages. (1) The reaction velocity decreases when the recycle solution is oxidized. (2) Recycle solutions which are kept for a long time are difficult to oxidize. Accordingly, the conventional processes for preparing DIX are not satisfactory. A need, therefore, continues to exist for a process for preparing DIX in a manner such that no decrease in the rate of reaction is observed.

SUMMARY OF THE INVENTION

Accordingly, one object of the present invention is to provide a process for preparing p-diisopropylbenzenedihydroperoxide by oxidizing the residual oil without decreasing the reaction rate.

Briefly, this object and other objects of the present invention as hereinafter will become more readily apparent can be attained by providing a process for preparing DIX by contacting DIPB with molecular oxygen, recovering DIX from the reaction mixture and recycling a residual oil which substantially contains DIPB and MOX, which is characterized by contacting the reaction mixture with an alkali metal hydroxide or an alkaline earth metal hydroxide and recovering DIX and recycling the residual oil. It is also possible to contact the residual oil with an alkali metal hydroxide or an alkaline earth metal hydroxide and then recycling the residual oil.

DETAILED DESCRIPTION OF THE PREFERRED EMBODIMENTS

The reaction of the present invention is conducted as described below.

DIPB or a mixture of DIBP and MOX is emulsified in an aqueous solution of sodium carbonate or sodium hydroxide and the emulsion is oxidized with air or oxygen. The oxidation reaction is preferably conducted at 90° – 100°C, especially 80°– 130°C under a pressure of 3 – 10 kg/cm$^2$ (gauge) of air in a volume ratio of the alkali solution to oil of 0.2 : 1 – 3 : 1, especially 0.5 : 1 –1 : 1. The concentration of the alkali solution is preferably about 3% $Na_2CO_3$ or about 0.5% NaOH. After the oxidation, the reaction mixture consists of a water phase and an oil phase. The oil phase contains the principal components of DIX, MOX, DIPB and high boiling point materials of unknown structure. The oil and water phases are separated from each other. DIX is separated from the oil phase by adding a DIX precipitating medium such as benzene which precipitates crystals consisting mostly of DIX and a solution is obtained which is suitable for recycling. DIX is separated from the medium by filtering. The medium solution is contacted with alkaline hydroxide, washed with water and then the medium is evaporated. The resulting recycle solution together with new DIPB if necessary, is repeatedly used for the oxidation reaction. Ther operation is repeated to prepare DIX from DIPB. Contact of the recycle solution with the alkaline hydroxide can be carried out in the medium. However, it is possible to directly contact the recycle solution prepared by evaporating the medium with the alkaline hydroxide.

Suitable DIX precipitating media include $C_{6-12}$ hydrocarbons such as toluene, DIPB, and the like as well as benzene. When cyclohexane or n-hexane is used as the DIX precipitating medium, the medium solution or the recycle solution prepared by evaporating the medium liquid can be contacted with the alkaline hydroxide. It is possible to contact the oil phase before precipitating DIX with the alkaline hydroxide.

The temperature of contact of the recycle solution with the alkaline hydroxide is not limited and is preferably in the range of room temperature at 80°C. If the temperature is too low, the required amount of the alkaline hydroxide required is large and the time required for contact is long. On the other hand, if the temperature is too high, the MOX in the recycle solution may be disadvantageously decomposed.

The pressure under which the reaction is conducted is preferably atmospheric. However, it is possible to use lower or higher pressures.

Suitable alkaline hydroxides for the reaction include alkali metal hydroxides such as sodium hydroxide and potassium hydroxide and alkaline earth metal hydroxides such as barium hydroxide, calcium hydroxide and magnesium hydroxide. The solid alkaline hydroxide is preferably used. However, an aqueous solution of the alkaline hydroxide can also be used. Of course, it is possible to use the alkaline hydroxide supported on a carrier such as silica gel, alumina or the like.

The amount of the alkaline hydroxide used depends upon the type and the condition of contact. A solid alkaline hydroxide can be contacted with recycle solution at room temperature to 90°C in amounts of 0.1 – 50 wt. %, preferably 1 – 30 wt. % of the alkaline hydroxide to the recycle solution. The amount of the alkali hydroxide to the recycle solution is usually in the range of 0.1 – 10 wt. %, preferably 1 – 3 wt. % in the case of potassium hydroxide; 1 – 50 wt. % preferably 10 – 30 wt. % in the case of sodium hydroxide; 1 – 30 wt. %, preferably 3 – 15 wt. % in the case of lithium hydroxide; and 10 – 50 wt. %, preferably 15 – 30 wt. % in the case of calcium hydroxide, magnesium hydroxide or barium hydroxide. It is possible to feed the recycle solution back to the reaction solution with washing with water after contacting it with the alkaline hydroxide, though the yield of DIX is slightly lowered. Accordingly, the recycle solution is preferably washed with water after contact with the base.

In the present process for oxidizing the recycle solution after contacting it with the alkaline hydroxide, the rate of reaction is not decreased and the yield of DIX is high. Recycle solution which is kept for a long time is difficult to oxidize. However, if the recycle solution has been in contact with alkaline hydroxide, it is easily oxidized.

The resulting DIX can be converted to hydroquinone by decomposing DIX in acetone with $H_2SO_4$. The hydroquinone is useful as a monomer polymerization inhibitor, as a developing agent for photography, as a rubber additive and the like. Accordingly, DIX, which is an intermediate of hydroquinone, can be prepared by a simple manner in high yield by the process of the present invention, whereby the cost of hydroquinone can be decreased.

Having generally described the invention, a more complete understanding can be obtained by reference to certain specific examples, which are included for purposes of illustration only and are not intended to be limiting unless otherwise specified.

EXAMPLE 1

Into a 20 liter autoclave equipped with a magnetic stirrer made of stainless steel SUS 32 were charged 4.9 kg of DIPB, 4.9 kg of water and 150 g of sodium carbonate. The autoclave was sealed and heated at 100°C. Air was charged into the autoclave to a pressure of 20 kg/cm² and the reaction was continued with stirring for 5.5 hours by feeding oxygen into the reaction vessel each time the pressure decreased 0.3 kg/cm². By this procedure a mixture of a water phase and an oil phase was obtained. The reaction mixture was mixed with 20 liters of benzene and the mixture was cooled to give 1.02 kg of crystals, a water phase and a benzene solution containing recycle solution.

The DIX and MOX in the crystals and the benzene solution were respectively decomposed by $H_2SO_4$ to give hydroquinone and isopropylphenol which were measured by gas chromatography. As a result, it was confirmed that the components of the reaction product were 92.2 wt. % DIX, 5.9 wt % MOX and 1.9 wt % of unknown materials. The components of the benzene solution except benzene were 18.7 wt % DIPB, 71.4 wt % MOX and 9.9 wt % unknown materials. A part of the benzene solution was sampled and was contacted with 10 g of solid sodium hydroxide at 50°C for 1 hour with stirring, and then the benzene solution was washed with water and benzene was evaporated to give 45.7 g of recycle solution. The recycle solution was admixed with 11.2 g of DIPB, 48.2 g of water and 1 g of sodium carbonate in a 200 cc autoclave equipped with a magnetic stirrer (made of stainless steel SUS 32). The autoclave was sealed and heated at 100°C. Air was charged into the vessel to a pressure of 20 kg/cm² and the reaction was continued with stirring for 2.5 hours. Each time the pressure decreased 0.3 kg/cm², oxygen was admitted. The reaction mixture separated into a water phase and an oil phase. The reaction mixture was mixed with 200 cc of benzene and the mixture was cooled to give 12.2 g of the crystals (11.3 g of DIX).

EXAMPLE 2

A portion of the benzene solution containing the recycle solution of Example 1 was sampled, and benzene was evaporated to give 46.1 g of the recycle solution. The recycle solution was contacted with 0.5 g of solid sodium hydroxide at room temperature for 15 mins with stirring, and then the mixture was filtered and the filtrate was admixed with 11.2 g of DIPB, 48.2 g of water and 1 g of sodium carbonate in a 200 cc autoclave and treated in accordance with the process of Example 1. By this procedure was obtained 12.3 g of crystals (11.5 g of DIX).

REFERENCE EXAMPLE 1

A portion of the benzene solution containing the recycle solution of Example 1 was sampled, and benzene was evaporated to give 45.9 g of the recycle solution. The recycle solution was admixed with 11.2 g of DIPB, 48.2 g of water and 1 g of sodium carbonate in a 200 cc autoclave, in accordance with process of Example 1. By this procedure was obtained 6.8 g of crystals (6.1 g of DIX).

EXAMPLE 3

A part of the benzene solution containing the recycle solution of Example 1 was sampled and benzene was evaporated to give 46.3 g of the recycle solution. The recycle solution was contacted with 10 g of solid calcium hydroxide at room temperature for one night with stirring, and then the mixture was filtered and the filtrate was admixed with 11.2 g of DIPB, 48.2 g of water and 1 g of sodium carbonate in a 200 cc autoclave and treated in accordance with the process of Example 1. By this procedure was obtained, 10.5 g of crystals (9.9 g of DIX).

EXAMPLE 4

The benzene solution containing the recycle solution of Example 1 was kept for 20 days and then was sampled. The benzene solution was contacted with 8 g of solid sodium hydroxide at 50°C for 2 hours with stirring, and then was washed with water. The benzene was evaporated to give 46.3 g of the recycle solution. The recycle solution was admixed with 11.2 g of DIPB. 48.2 g of water and 1 g of sodium carbonate in a 200 cc autoclave and treated in accordance with the process of Example 1. By this procedure was obtained 11.8 g of crystals (10.7 g of DIX).

EXAMPLE 5

The benzene solution containing the recycle solution of Example 1 was kept for 20 days and then was sampled. The benzene was evaporated to give 46.2 g of the recycle solution. The recycle solution was contacted with 3 g of solid lithium hydroxide at 50°C for 3 hours with stirring, and the mixture was filtered. The filtrate was admixed with 11.2 g of DIPB, 48.2 g of water and 1 g of sodium carbonate in a 200 cc autoclave and treated in accordance with the process of Example 1. By this procedure was obtained 12.1 g of crystals (11.5 g of DIX).

EXAMPLE 6

The benzene solution containing the recycle solution of Example 1 was kept for 20 days and then was sampled. The benzene solution was washed with 5% aqueous sodium hydroxide solution and further washed with water. The benzene was evaporated to give 45.1 g of the recycle solution. The recycle solution was admixed with 11.2 g of DIPB, 48.2 g of water and 1 g of sodium carbonate in a 200 cc autoclave and treated in accordance with the process of Example 1. By this procedure was obtained 11.5 g of crystals (11.0 g of DIX).

REFERENCE EXAMPLE 2

The benzene solution containing the recycle solution of Example 1 was kept for 20 days and then sampled. The benzene was evaporated to give 46.6 g of the recycle solution. The recycle solution was admixed with 11.2 g of DIPB, 48.2 g of water and 1 g of sodium carbonate in a 200 cc autoclave and was treated in accordance with the process of Example 1 to give 0.8 g of crystals.

EXAMPLE 7

Into a 20 liter autoclave equipped with a magnetic stirrer of stainless steel SUS 32 were charged 4.9 kg of DIPB, 4.9 kg of water and 150 g of sodium carbonate and the autoclave was sealed and heated to 90°C. Air was charged into the vessel at a pressure of 20 kg/cm$^2$ and the reaction was continued with stirring for 8.5 hours. Oxygen was fed into the autoclave each time the pressure decreased 0.3 kg/cm$^2$. The reaction mixture separated into a water phase and an oil phase. The oil phase was separated from the water phase, and 60 g of the oily material was sampled and was contacted with 1 g of solid sodium hydroxide at 80°C for 30 minutes with stirring and the mixture was filtered. The filtrate was admixed with 200 cc of cyclohexane and the mixture was cooled to room temperature to give a cyclohexane solution containing 11.3 g of crystals (10.7 g of DIX) and a recycle solution. The crystals were filtered and cyclohexane was evaporated to give 47.2 g of the recycle solution. The recycle solution was admixed with 12 g of DIPB, 35 cc of water and 1 g of sodium carbonate in a 200 cc autoclave equipped with a magnetic stirrer made of stainless steel SUS 32. The autoclave was sealed and heated at 90°C and air was charged to a pressure of 20 kg/cm$^2$. The reaction mixture was continually stirred for 6 hours by feeding oxygen into the autoclave each time the pressure decreased 0.3 kg/cm$^2$. The reaction mixture separated into a water phase and an oil phase. The reaction mixture was mixed with 200 cc of cyclohexane and the mixture was cooled to give 13.1 g of crystals (12.8 g of DIX).

EXAMPLE 8

A 60 g amount of the oily material of Example 7 was sampled and was admixed with 200 cc of cyclohexane. The mixture was cooled to room temperature to give a cyclohexane solution containing 12.0 g of crystals (11.6 g of DIX) and the recycle solution. The cyclohexane solution was contacted with 8 g of solid sodium hydroxide at 50°C for 1 hour with stirring, and the mixture was filtered. The filtrate was washed with water and cyclohexane was evaporated to give 46.1 g of the recycle solution. The recycle solution was admixed with 12 g of DIPB, 35 cc of water and 1 g of sodium carbonate in a 200 cc autoclave and treated in accordance with the process of Example 7 to give 12.2 g of crystals (11.8 g of DIX).

REFERENCE EXAMPLE 3

A 60 g amount of the oily material of Example 7 was sampled and admixed with 200 cc of cyclohexane. The mixture was cooled to room temperature to give a cyclohexane solution containing 11.8 g of crystals (11.2 g of DIX), and the recycle solution. The crystals were filtered and cyclohexane was evaporated from the filtrate to give 47 g of the recycle solution. The recycle solution was admixed with 12 g of DIPB, 35 cc of water and 1 g of sodium carbonate in a 200 cc autoclave and treated in accordance with the process of Example 7 to give 6.3 g of crystals (6.0 g of DIX).

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for preparing p-diisopropylbenzenedihydroperoxide by contacting p-diisopropylbenzene with molecular oxygen in an aqueous, emulsified reaction mixture, separating p-diisopropylbenzenedihydroperoxide from the reaction mixture and recycling a non-aqueous residual solution containing p-diisopropylbenzene and p-diisopropylbenzene monohydroperoxide, the improvement which comprises:

contacting said reaction mixture with a $C_{6-12}$ hydrocarbon precipitating medium thereby precipitating said p-diisopropylbenzenedihydroperoxide from said reaction mixture and forming an aqueous phase and a medium solution containing said precipitating medium, p-diisopropylbenzene and p-diisopropylbenzene monohydroperoxide;

contacting the medium solution separated from the p-diisopropylbenzene-dihydroperoxide precipitate with a solid alkali metal hydroxide or a solid alkaline earth metal hydroxide at room temperature to 90°C;

evaporating the precipitating medium; and recycling the residual solution.

2. The process of claim 1, wherein said medium solution is stored for a long time prior to contact with said solid alkali metal hydroxide or alkaline earth metal hydroxide.

3. The process of claim 1, wherein the medium is benzene, cyclohexane, n-hexane, toluene or diisopropylbenzene.

4. In a process for preparing p-diisopropylbenzenedihydroperoxide by contacting p-diisopropylbenzene with molecular oxygen in an aqueous, emulsified reaction mixture, separating p-diisopropylbenzenedihydroperoxide from the reaction mixture and recycling a non-aqueous residual solution containing p-diisopropylbenzene and p-diisopropylbenzenemonohydroperoxide, the improvement which comprises:

contacting said reaction mixture with a $C_{6-12}$ hydrocarbon precipitating medium thereby precipitating said p-diisopropylbenzenedihydroperoxide from said reaction mixture and forming an aqueous phase and a medium solution containing said precipitating medium, p-diisopropylbenzene and p-diisopropylbenzenemonohydroperoxide;

evaporating the medium from said medium solution separated from said precipitate;

contacting the residual solution with a solid alkali metal hydroxide or alkaline earth metal hydroxide at room temperature to 90°C; and recycling said residual solution.

5. The process of claim 4, wherein said medium is benzene, cyclohexane, n-hexane, toluene or diisopropylbenzene.

6. The process of claim 4, wherein said residual solution prepared by evaporating the medium from said medium solution is stored for a long time prior to contact with said alkali metal hydroxide or alkaline earth metal hydroxide.

7. In a process for preparing p-diisopropylbenzenedihydroperoxide by contacting p-diisopropylbenzene with molecular oxygen in an aqueous, emulsified reaction mixture, separating p-diisopropylbenzenedihydroperoxide from the reaction mixture and recycling a non-aqueous residual solution containing p-diisopropylbenzene and p-diisopropylbenzenemonohydroperoxide, the improvement which comprises:

separating the oil phase and aqueous phase of said reaction mixture;

contacting said oil phase with a $C_{6-12}$ hydrocarbonn precipitating medium to precipitate p-diisopropylbenzenedihydroperoxide therefrom;

contacting the medium solution containing said precipitating medium with a solid alkali metal hydroxide or alkaline earth metal hydroxide at room temperature to 90°C;

evaporating the medium from said medium solution; and recycling said residual solution.

8. The process of claim 7, wherein said medium is benzene, cyclohexane, n-hexane, toluene or diisopropylbenzene.

9. The process of claim 7, wherein said medium solution is stored for a long time prior to contact with said alkali metal hydroxide or alkaline earth metal hydroxide.

10. In a process for preparing p-diisopropylbenzenedihydroperoxide by contacting p-diisopropylbenzene with molecular oxygen in an aqueous, emulsified reaction mixture, separating p-diisopropylbenzenedihydroperoxide from the reaction mixture and recycling a non-aqueous residual solution containing p-diisopropylbenzene and p-diisopropylbenzenemonohydroperoxide, the improvement which comprises:

separating the oil phase and aqueous phase of said reaction mixture;

contacting said oil phase with a $C_{6-12}$ hydrocarbon precipitating medium to precipitate p-diisopropylbenzenedihydroperoxide therefrom;

evaporating the hydrocarbon precipitating medium from said oil phase separated from the precipitated p-diisopropylbenzenedihydroperoxide;

contacting the residual solution with a solid alkaline metal hydroxide or solid alkaline earth metal hydroxide at room temperature to 90°C; and recycling said contacted residual solution.

11. The process of claim 10, wherein said medium is benzene, cyclohexane, -hexane, toluene or diisopropylbenzene.

12. The process of claim 10, wherein the medium solution is stored for a long time prior to evaporation of the medium from said medium solution.

13. In a process for preparing p-diisopropylbenzenedihydroperoxide by contacting p-diisopropylbenzene with molecular oxygen to form an aqueous, emulsified reaction mixture, separating the resultant oil and aqueous phases, separating p-diisopropylbenzenedihydroperoxide from said oil phase, and recycling a non-aqueous residual solution containing p-diisopropylbenzene and p-diisopropylbenzenemonohydroperoxide, the improvement which comprises:

contacting said oil phase with a solid alkali metal hydroxide or a solid alkaine earth metal hydroxide at room temperature to 90°C; and then precipitating said p-diisopropylbenzenedihydroperoxide from said contacted reaction mixture by subjecting said reaction mixture to a $C_{6-12}$ hydrocarbon precipitating medium.

14. The process of claim 13, wherein said medium is benzene, cyclohexane, n-hexane, toluene or diisopropylbenzene.

* * * * *